United States Patent [19]

Bennes et al.

[11] Patent Number: 5,669,884
[45] Date of Patent: Sep. 23, 1997

[54] TUCK-AWAY BELT FOR PERITONEAL DIALYSIS PATIENTS

[76] Inventors: Solita M. Bennes, 199 Highland St., Valparaiso, Fla. 32580; Cathy Dickson, 4535 Nancy Ward La., Niceville, Fla. 32578

[21] Appl. No.: 526,167

[22] Filed: Sep. 11, 1995

[51] Int. Cl.⁶ .................................................. A61M 5/32
[52] U.S. Cl. ........................................ 604/179; 604/174
[58] Field of Search .................................. 604/174, 179, 604/180; 128/DIG. 26; 2/311

[56] References Cited

U.S. PATENT DOCUMENTS

| | | | |
|---|---|---|---|
| 4,569,348 | 2/1986 | Hasslinger et al. | 604/179 |
| 4,591,356 | 5/1986 | Christie | 604/179 |
| 4,596,560 | 6/1986 | Simpson . | |
| 4,666,432 | 5/1987 | McNeish et al. | 604/174 X |
| 4,738,661 | 4/1988 | Marut . | |
| 4,955,867 | 9/1990 | Endo . | |
| 5,048,512 | 9/1991 | Turner et al. | 604/179 X |
| 5,244,464 | 9/1993 | Madden et al. | 604/179 |
| 5,304,145 | 4/1994 | Blair | 604/179 |
| 5,403,285 | 4/1995 | Roberts | 604/179 |
| 5,425,719 | 6/1995 | Lessing, Jr. | 604/179 |
| 5,468,229 | 11/1995 | Chandler | 604/179 |

*Primary Examiner*—Sam Rimell

[57] ABSTRACT

A fabric of flexible material adapted to be worn around the abdomen of a patient adjacent to the protruding end of a Peritoneal Dialysis catheter and transfer tube. The front part of the belt that crosses the abdomen consists of a single panel of fabric, the back part of the main belt is made up of two pieces of fabric layered one on top of the other forming a reinforced envelope into which the transfer tube is inserted. The rest of the belt is made of an elastic band attached to each end of the main belt and featuring a fastening means. This belt serves to enclose, protect, and secure the transfer tube and prevent it from dangling. The proposed device, Tuck-Away Belt, accommodates this transfer tube, is not restrictive to active Peritoneal Dialysis patients, and is not noticeable under conventional garment. This proposed device enhances a patient's self esteem and self confidence because the transfer tube is safely tucked away underneath the garment and not easily detected, avoiding potential embarrassing situations.

1 Claim, 3 Drawing Sheets

TUCK-AWAY BELT FOR PERITONEAL DIALYSIS PATIENTS

BACKGROUND OF THE INVENTION

1. Background—Field of Invention

The present invention relates generally to medical appliances and more specifically to a belt for use on patients who have had a Peritoneal Dialysis surgical procedure performed. The device within the scope of the present invention is economical to fabricate and easy to use. The device can be easily removed, worn during baths and showers, and washed frequently to maintain cleanliness and sanitary condition around the point of insertion of the Peritoneal Dialysis surgical procedure.

2. Background—Description of Prior Art

Prior arts exist with many surgical drains, belts, and appliances in order to make a patient more comfortable after having undergone a surgical procedure of one type or the other. The following constitutes our patent search for these prior arts. We found no other evidence that the proposed patent infringes on any other patent and the tuck-away belt provides a unique design. Many appliances have been designed for use on patients having gone through a gastrostomy or peritoneal dialysis procedure such as U.S. Pat. No. 4,738,661 issued to Marie R. Marut on Apr. 19, 1988, for a gastrostomy belt; U.S. Pat. No. 4,596,560 issued to Mary Simpson on Jun. 24, 1986, for a gastrostomy tube protector; and U.S. Pat. No. 4,044,867, issued to Walter Endo on Sep. 11, 1990, for a peritoneal dialysis catheter protector belt.

U.S. Pat. No. 4,044,867 device is specifically designed for patients who have undergone peritoneal dialysis surgical procedure where a catheter is implanted into the peritoneal cavity of a patient and protrudes out of the abdomen about 4 inches. This device, however, is outdated. It was created by the inventor to accommodate a 4-inch catheter. Since this time and this patent, a transfer tube has been designed and implemented; the transfer tube is attached to the end of the 4-inch catheter which extends out of the abdomen. The proposed device, Tuck-Away Belt, accommodates the transfer tube, is not restrictive to active Peritoneal Dialysis patients, and is not noticeable under conventional clothing.

For a long time Hemodialysis was the only treatment of renal failure available. This treatment procedure is done at a Dialysis Center where a patient's blood is removed and passed through a dialysis machine which cleans the blood of waste. The patient's blood is circulated and cleansed outside the body. The blood is withdrawn through a needle inserted in a blood vessel in the patient's arm or leg. The needle is attached by plastic tubing to a Hemodialysis machine. The machine pumps the patient's blood out of the body and through a dialyzer containing a synthetic semipermeable membrane. The Hemodialysis machine keeps the blood moving through the dialyzer while waste fluid are being filtered out. The Hemodialysis machine then returns the cleansed blood to the patient through a second needle in the same blood vessel. Patients who need long-term Hemodialysis treatment are connected to a dialysis machine for 4 to 6 hours at a time two or three times a week.

Peritoneal Dialysis on the other hand, has only been in use over the past decade and is considered a medical breakthrough in the treatment of renal failure. Peritoneal Dialysis functions the same way kidneys do by constantly cleansing the blood as long as there is dialysis fluid in the peritoneal cavity. The dialysis fluid is left in the peritoneal cavity for several hours to collect waste from the blood. The used dialysis fluid is drained from the cavity into a drain bag and replaced with fresh dialysis fluid. This dialysis treatment procedure called an exchange is done through the catheter. A few years ago, a transfer tube set was devised to make dialysis treatment more manageable. The transfer tube is about 8 inches long, flexible, and made of soft plastic with a clamp at the end. The tube is capped for protection from gems and diseases.

The catheter is surgically inserted inside the abdominal cavity of a peritoneal patient and extends out of the abdomen about 4 inches. The exit site from which the catheter extends is located about 4 inches parallel from either side of the navel. The transfer tube attached to the end of the extended catheter provides an opening through which dialysis fluid can be instilled into the abdominal cavity. The abdominal cavity is used as a reservoir for the dialysis fluid. Waste products pass from the blood stream, through the peritoneal membrane, and into the dialysis fluid. The old dialysis fluid is periodically drained from the abdominal cavity and replaced with fresh dialysis fluid.

The protruding end of the transfer tube, which extends about 8 inches dangles loosely from the abdomen when not in use. The dangling transfer tube is likely to become tangled in the patient's clothing and cause unsightly bulges. Also, the danger that the dangling transfer tube may be caught in furniture or other objects could result in painful consequences and internal bleeding. One practice is to tape the transfer tube to the abdomen; however, this method of securing the transfer tube can irritate a patient's skin and the tape doesn't keep the tube attached to the abdomen for very long. When this happens, the transfer tube drops and the weight of the tube alone is very painful to the patient.

OBJECTS AND ADVANTAGES

The object of this invention is to provide a device to serve as a safe storage area for the transfer tube set when not in use.

It is the object of the present invention to provide a belt which is newer in design to accommodate the additional length of the transfer tube attached to the catheter. The envelope in which the transfer tube is inserted is wide enough to facilitate inserting and retrieving the tube during an exchange procedure.

Another object of the present invention is to provide an inexpensive, reusable belt, comfortable for a patient to wear and hide any obtrusive portion of the transfer tube that can otherwise be visibly detected when worn with conventional garments.

Another object of this invention is to provide a readily adjustable and an easily changeable belt for use on patients having had a peritoneal surgical procedure performed.

Yet another object of this invention is to provide a simple and inexpensive Peritoneal Dialysis belt which is a durable product.

A further object of this invention is to provide a belt which is reusable, washable, may be washed repeatedly, and can be worn while bathing so the transfer tube is not allowed to dangle.

Because part of the belt is elasticized, another object is to provide easy access to the transfer tube from its location when an exchange is to be performed. The transfer tube is easily retrieved from its storage device, returned, and safely stored and tucked away in this belt after an exchange. This is a belt which is convenient to use when an exchange is to be performed and can even be used at the patient's place of employment.

The object of this invention is to provide a belt having an elastic band as the back portion to allow body movement and to fit smoothly with the contour of a patient's body.

Another object of this invention is to provide a belt to be worn around the lower part of the protruding abdomen of the patient to prevent bulkiness under garments. Peritoneal dialysis patients characteristically have an inflated stomach because of the instilled dialysis fluid. The belt is equipped with an envelope opening for inserting the protruding transfer tube.

The object of this invention is to provide a belt which enhances a patient's-self esteem and self confidence because the transfer tube is safely tucked away underneath the garment and not easily detected avoiding potential embarrassing situations.

SUMMARY OF THE INVENTION

More and more patients with kidney failures are opting for peritoneal dialysis treatment because it allows them more mobility. Peritoneal Dialysis treatment gives them the freedom to occupy themselves during a treatment. Working people experience no loss of work days because an exchange can be done at their place of employment. A person doing an exchange at work can easily access the transfer tube from its storage area, the Tuck-Away Belt. When Peritoneal Dialysis was first implemented a decade ago, about 50,000 patients entered the program. The number of patients has grown since that time and the numbers are still growing.

A proposed device, Tuck-Away Belt, for use on a patient having been subjected to a peritoneal dialysis surgical procedure. A transfer tube is attached to the surgically implanted catheter to make dialysis procedure more manageable. This belt accommodates the transfer tube, is not restrictive to active peritoneal dialysis patients, and is not noticeable under conventional clothing. This proposed device enhances a patient's self esteem and self confidence because the transfer tube is safely tucked away underneath the garment and not easily detected, avoiding potential embarrassing situations.

The belt is a single one-piece device. The front part of the panel which is away from the patient's body is a single piece of soft, smooth fabric and crosses the abdomen. The back part of the panel is made of two pieces of fabric layered one on top of the other forming a reinforced envelope into which the transfer tube is inserted when not in use. The finished cotton panel is three layers thick. Attached to the narrow ends of this compound panel is an elastic band which passes around the body of the patient with closure means attached to each end. The closure means can include hooks and several loops on each end, or a Velcro strap and rings, making for generic sizing.

Figure 1:
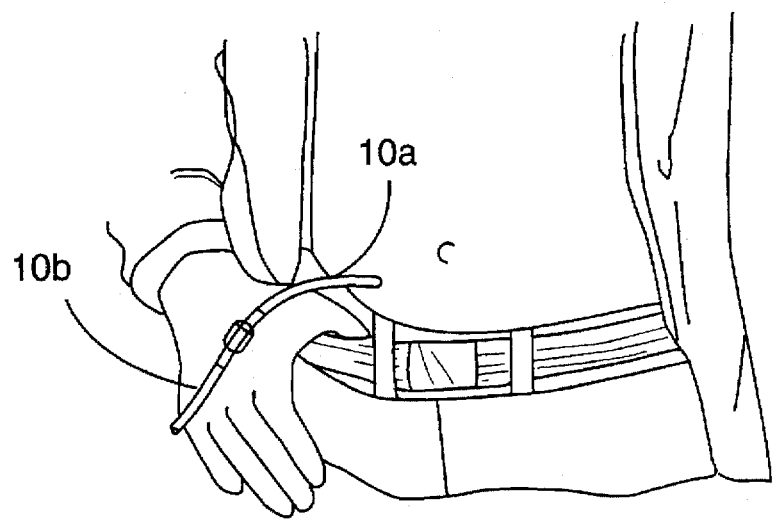
FIG. 1 shows the exit site on a patient with a 4-inch catheter extending out of the abdomen with a transfer tube attached to the catheter.

REFERENCE NUMERALS IN DRAWINGS 10a catheter 10b transfer tube
12 disposable tubing set 14a drain bag
14b new fluid in collapsible bag 20 front panel
22 opening on inside panel 24 elastic band
26 hook 28 loops

NARRATIVE DESCRIPTION

Figure 2:
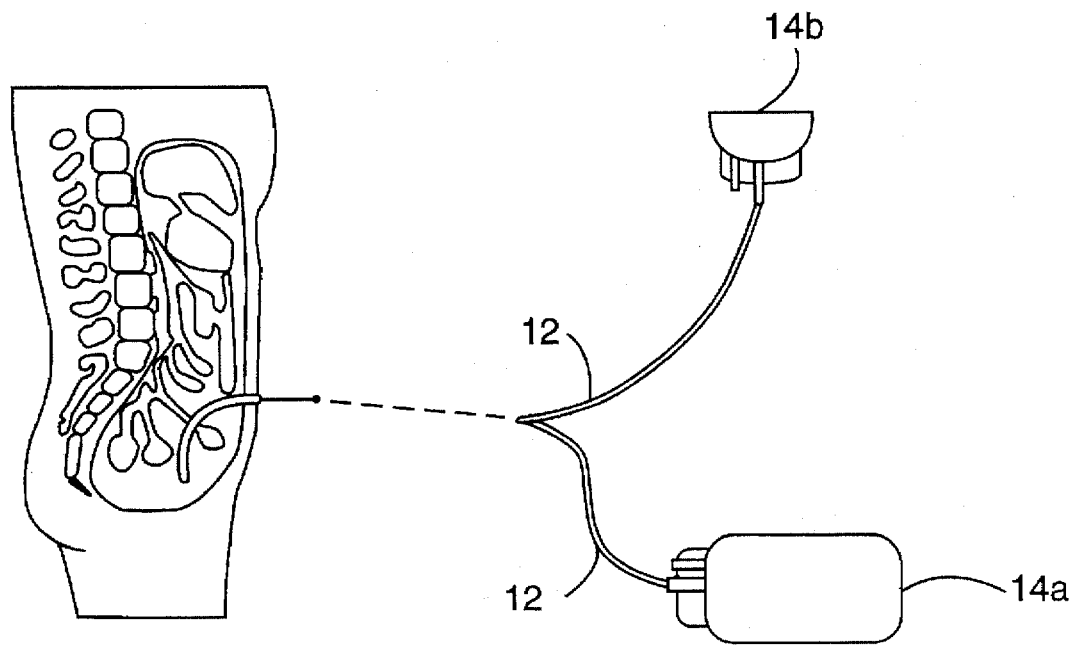
FIG. 2 shows the peritoneal cavity filled with new fluid which is allowed to dwell for a period of time to remove wastes from the blood.
Figure 3:
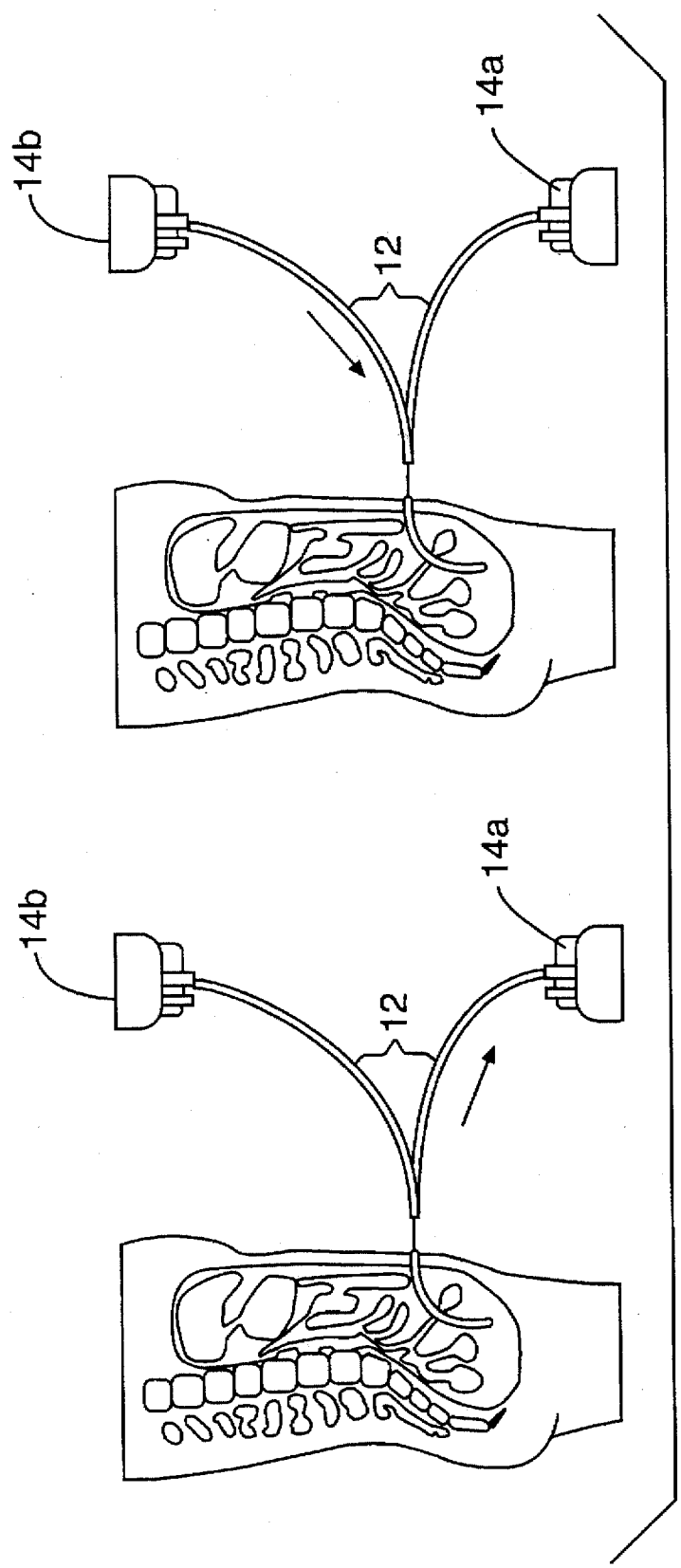
FIG. 3 shows the transfer of old fluid out of the peritoneal cavity and new fluid.

FIG. 1 shows the area of the exit site with a 4-inch catheter extending out of the abdomen 10a and a transfer tube 10b attached to it. The instilled dialysis fluid in the abdominal cavity is allowed to dwell for many hours to remove wastes from the blood through the peritoneum, a thin layer of tissue that lines the stomach cavity, as shown in FIG. 2. During the peritoneal dialysis treatment procedure, a patient connects to a disposable tubing set called a Y 12 which allows old fluid to drain into a drain bag 14a and allows new fluid in another bag 14b to flow into the abdominal cavity. FIG. 3 shows the transfer of old fluid from the peritoneal cavity to new fluid flowing through the Y 12. The old fluid is drained into a drain bag 14a and the new fluid from a collapsible bag 14b fills the peritoneal cavity.

Figure 4:
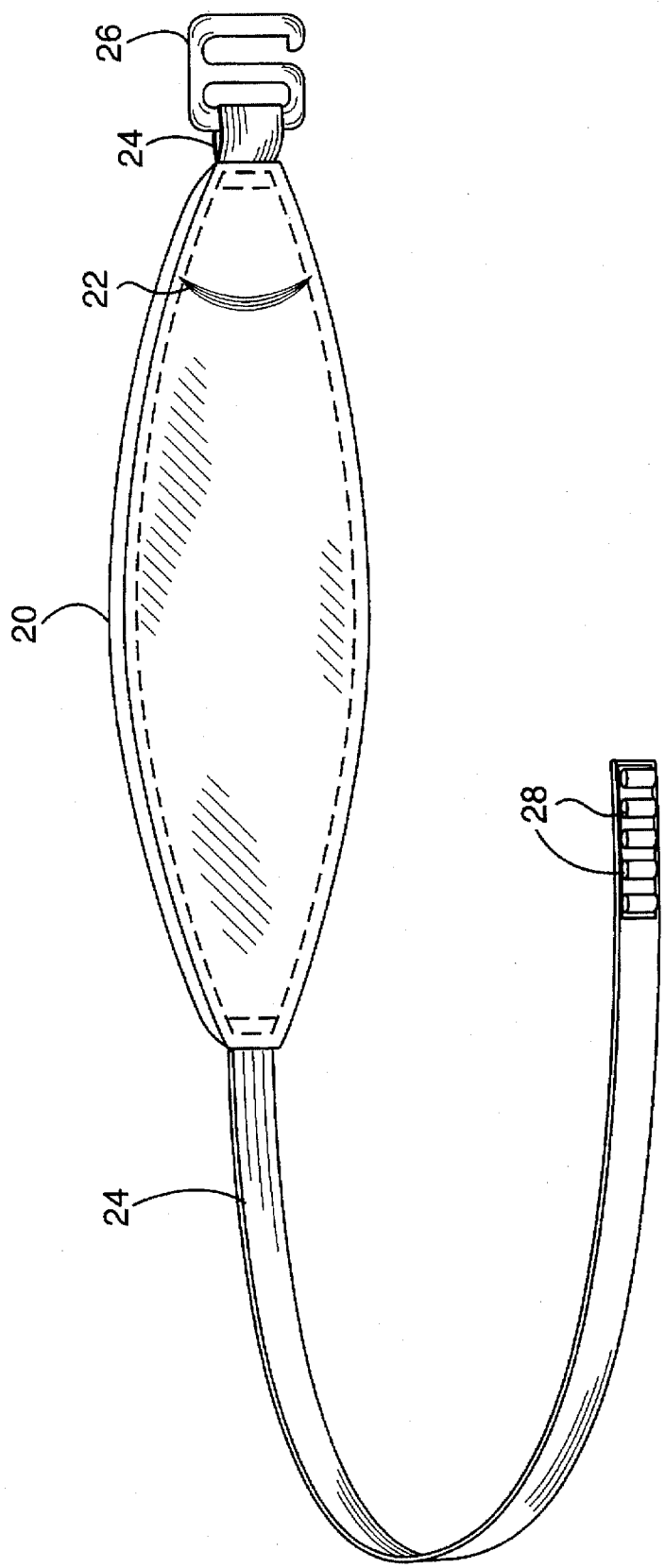
FIG. 4 is a perspective representation of a belt constructed in accordance with the concepts of the present document.

When an exchange is completed, the solution bag 14b, disposable tube set 12, and drain bag 14a are detached from the transfer tube and disposed of, and the transfer tube is then capped, stored, and tucked away in the belt, FIG. 4.

According to this invention, a belt, FIG. 4, is worn around the lower part of the abdomen of the patient and fastened at the ends of the belt. There are various attachment mechanisms to be employed such as Velcro or hook on one end of the elastic and several loops sewn at the other end of the elastic band for generic sizing. The belt, FIG. 4, is made of a single one-piece device. Part of the belt that crosses the abdomen is made of three soft flexible panels. The front panel 20 is a solid piece of fabric and self-lined. The back panel is made of two pieces of fabric layered one on top of the other forming a reinforced envelope 22 into which the transfer tube is inserted when not in use. Attached to the narrow ends of this panel is an elastic band 24 which passes around the body of the patient. The belt can be fastened with a hook 26 one end of the elastic and several loops 28 on the other making for generic sizing.

CONCLUSION

The Tuck-Away Belt, FIG. 4, is constructed from a flexible cotton or like material to allow for easy insertion and retrieval of the transfer tube when an exchange is to be performed. The device within the scope of the present invention is economical to fabricate and easy to use. The device can be easily removed, worn during baths and showers, and washed frequently to maintain cleanliness and sanitary condition around the exit site.

The device provides a convenient means for retaining and storing the transfer tube, so as to overcome the inconveniences and painful disadvantages by permitting the end of the transfer tube to dangle from the patient.

We claim:

1. A Tuck Away belt for holding a dialysis transfer tube comprising:

A flexible, elongated pocket having a first end and a second end, an upper side and a lower side, the pocket including a first outer panel formed from a flexible, self lined material having a first horizontal length, and a second panel attached to the first panel along said upper and lower sides and along one of said ends and having a second horizontal length, the second horizontal length being less than the first horizontal length so as to define an opening having a fixed width between the first and second panels capable of accommodating a dialysis transfer tube;

a flexible elastic belt fixedly attached to the first end and the second end of said pocket, one end of said belt having at hook attachment and an opposite end of said belt having multiple loop attachments;

wherein said width of said opening is greater than the width of said belt so as to accommodate insertion and removal of the transfer tube.

* * * * *